United States Patent [19]

Wu

[11] Patent Number: 5,130,458
[45] Date of Patent: Jul. 14, 1992

[54] PREPARATION OF BIS(1,5-CYCLOOCTADIENE)NICKEL(O)

[75] Inventor: An-hsiang Wu, Bartlesville, Okla.

[73] Assignee: Phillips Petroleum Company, Bartlesville, Okla.

[21] Appl. No.: 784,500

[22] Filed: Oct. 29, 1991

[51] Int. Cl.$^5$ .............................................. C07F 15/04
[52] U.S. Cl. ..................................... 556/143; 556/138
[58] Field of Search .................................. 556/143, 138

[56] References Cited

U.S. PATENT DOCUMENTS

| | | | |
|---|---|---|---|
| 3,300,472 | 1/1967 | Kleiman et al. | 556/143 X |
| 3,490,745 | 1/1970 | Chappell, III et al. | 252/430 |
| 3,657,297 | 4/1972 | Spicer et al. | 556/143 |
| 4,518,814 | 3/1985 | Knudsen et al. | 585/523 |
| 5,059,701 | 10/1991 | Keipert | 556/143 X |

OTHER PUBLICATIONS

"Olefin-Komplexe des Nickel(O)", by B. Bogdanovic et al., Annular der Chemie, 699, 1966, pp. 1–23.

Primary Examiner—Arthur C. Prescott
Attorney, Agent, or Firm—K. K. Brandes

[57] ABSTRACT

The preparation of bis(1,5-cyclooctadiene)nickel(O) from nickel(II) acetylacetonate and 1,5-cyclooctadiene in the presence of at least one alkylaluminum compound (preferably triethylaluminum) is carried out in the substantial absence of added butadiene with nickel(II) acetylacetonate hydrate, wherein the molar ratio of the alkylaluminum compound to the nickel(II) acetylacetonate hydrate is at least about 1.5:1.

18 Claims, No Drawings

PREPARATION OF BIS(1,5-CYCLOOCTADIENE)NICKEL(O)

BACKGROUND OF THE INVENTION

This invention relates to the synthesis of bis(1,5-cyclooctadiene)Ni(O), which is useful as an intermediate in the preparation of ethylene oligomerization catalysts.

An article is Annalen der Chemie, 699, 1966, pages 1-23 describes the synthesis of bis(1,5-cyclooctadiene)-Ni(O) from Ni acetylacetonate and 1,5-cyclooctadiene in the presence of butadiene. The present invention is directed to a simplified method of cynthesizing bis(1,5-cyclooctadiene)Ni(O) which does not require the presence of butadiene.

SUMMARY OF THE INVENTION

It is an object of this invention to prepare bis(1,5-cyclooctadiene)nickel(O) in the substantial absence of butadiene. Other objects and advantages will be apparent from the detailed description of the invention and the appended claims.

According to this invention, in a process for preparing bis(1,5-cyclooctadiene)nickel(O) from nickel (II) acetylacetonate and 1,5-cyclooctadiene in the presence of at least one alkylaluminum compound, the improvements comprise: (a) the use of a nickel(II) acetylacetonate hydrate, (b) a molar ratio of said at least one alkylaluminum compound to said nickel(II) acetylacetonate hydrate of at least about 1.5:1, and (c) the substantial absence of added butadiene (i.e., 1,2-butadiene and/or 1,3-butadiene).

In a preferred embodiment, the at least one alkylaluminum compound is at least one trialkylaluminum with each alkyl group being independently selected from alkyl groups containing 1-8 carbon atoms. In another preferred embodiment, the molar ratio of the alkylaluminum compound to Ni(II) acetylacetonate hydrate is in the range of about 1.5:1 to about 5:1.

DETAILED DESCRIPTION OF THE INVENTION

The principal process ingredients employed in the process of this invention are known. Nickel(II) acetylacetonate hydrate is commercially available, e.g., as dihydrate from the Laboratory and Research Division of Eastman Kodak Company, Rochester, NY. Other suppliers include Alfa Products Division of Johnson Mathey, Inc., Danvers, MA; and Shepherd Chemical Company, Cincinnati, OH. This compound can also be prepared by the reaction of nickel hydroxide and 2,4-pentanedione. 1,5-cyclooctadiene is commercially available from Eastman Kodak Company, or it can be prepared by dimerization of 1,3-butadiene.

Alkylaluminum compounds which are also employed in the process of this invention, such as triethylaluminum, are commercially available from (among others) the Chemicals Group of Ethyl Corporation, Orangeburg, SC, or the CVD subsidiary of Morton International, Inc., Woburn, MA; or Texas Alkyls, Inc., Deer Part, TX. Other suitable trialkylaluminum compounds, such as trimethylaluminum, tri-n-butylaluminum, triisobutylaluminum, tri-n-hexylaluminum, tri-n-octylaluminum, dimethylaluminum hydride, diisobutylaluminum hydride, diethylaluminum chloride, diethylaluminum iodide, diethylaluminum ethoxide, diisobutylaluminum chloride, di-n-octylaluminum iodide, ethylaluminum dichloride, ethylaluminum sesquichloride, isobutylaluminum dichloride, and the like are also commercially available from the above-mentioned and/or other chemical companies.

Ni(II) acetylacetonate hydrate, 1,5-cyclooctadiene and at least one alkylaluminum compound can be mixed in any suitable manner and in suitable order. The entire procedure is carried out in a dry, inert atmosphere. Generally, a solution of a suitable alkylaluminum compound, preferably triethylaluminum dissolved in an aromatic hydrocarbon (preferably benzene or toluene), is added to a mixture of the Ni(II)acetylacetonate hydrate and 1,5-cyclooctadiene in a suitable organic solvent (preferably benzene or toluene) which has been cooled to a temperature not to exceed about 0° C. (i.e., about 0° C. or below), preferably to a temperature of about −80° C. to about 0° C. Generally, the addition of dissolved alkylaluminum to Ni(II) acetylacetonate hydrate and 1,5-cyclooctadiene requires a period of time of at least about 1 minute, preferably about 2-60 minutes, more preferably about 5-30 minutes, and is generally carried out with agitation (preferably stirring) under a dry, inert gas atmosphere (preferably dry $N_2$ or He or Ar).

Any suitable concentrations of the solutions can be employed, preferably about 1-10 mole/l of 1,5-cyclooctadiene and about 0.5-3 mole/l of the alkylaluminum compound(s). Any suitable molar ratios of the process ingredients can be employed. It is a critical feature of this invention to employ a molar ratio of the at least one alkylaluminum compound to Ni(II) acetylacetonate hydrate of at least about 1.5:1, preferably about 1.5:1 to about 5:1, more preferably about 1.8:1 to about 2.5:1. The molar ratio of 1,5-cyclooctadiene to the Ni(II) acetylacetonate hydrate generally is in the range of about 1:1 to about 20:1, preferably about 4:1 to about 8:1.

After the addition of the dissolved alkylaluminum has been completed, the reaction mixture is generally heated, with agitation (such as stirring), to a temperature above about 0° C. (preferably about 5°-50° C., more preferably about 10°-30° C.) for a period of time required to substantially complete the reaction, under an inert gas atmosphere. Generally, the reaction time is in the range of about 10 minutes to about 20 hours, depending on the reaction conditions, such as reaction temperature, extent of agitation and the like. Butadiene (or any other ethylenically-unsaturated hydrocarbon which can act as a Lewis base) is substantially absent from the reaction mixture.

The completed reaction mixture is generally filtered so as to separate the solid, crystalline bis(1,5-cyclooctadiene)nickel(O) therefrom, which can be purified by washing with a suitable liquid, such as an aromatic hydrocarbon and/or an ether. Optionally, bis(1,5-cyclooctadine)Ni(O) can be further purified by recrystallization employing any suitable solvent, preferably toluene.

The following examples are provided to further illustrate the process of this invention and its advantages over prior art process, and are not to be construed as unduly limiting the scope of this invention.

EXAMPLE I

This example illustrates the preparation of bis(1,5-cyclooctadiene)nickel(O) from anhydrous Ni(II) acetylacetomate.

The first preparation procedure was carried out substantially in accordance with the procedure described in Annalen der Chemie, 1966, 699, page 16. A solution of 129 g (1.13 mol) triethylaluminum (TEA) in 260 ml of dry benzene was slowly added to a cold (−5 to −2° C.) mixture of 280 g (1.09 mol) of anhydrous nickel (II) acetylacetonate, 590 g (5.45 mol) of freshly distilled 1,5-cyclooctadiene and 25 g (0.46 mol) 1,3-butadiene in 800 mL of dry benzene. This slow addition of the TEA solution was carried out under an argon atmosphere over a period of 4–5 hours with stirring, while cooling the entire reaction mixture with an external $NH_4Cl$/ice bath, so as to maintain a temperature of about −5 to about −2° C. After the TEA addition had been completed, the $NH_4Cl$/ice bath was removed, and the reaction mixture was stirred for at about 20 hours room temperature under an argon gas atmosphere. The reaction mixture was then filtered, the filter cake was washed twice with 250 mL of cold benzene and then twice with 250 mL of cold diethyl ether. The washed bright-yellow, microcrystalline bis(1,5-cyclooctadiene)-Ni(O) was dried under vacuum conditions and weighed. The yield of dry bis(1,5-cyclooctadiene)Ni(O), which melted with decomposition under an Ar atmosphere at 142° C., was 267 g (0.97 mol), corresponding to an 89% yield based on Ni(II) acetylacetonate. A second preparation, which was carried out substantially in accordance with the above-described method, except that the temperature during the TEA addition was −78° C., also resulted in a product yield of 89%.

A third control procedure was carried out with anhydrous Ni(II) acetylacetonate without the addition of 1,3-butadiene. 15 mL of a 1.9 molar TEA solution is toluene was added within a period of 5 minutes to a mixture of 7.0 g anhydrous Ni(II) acetylacetonate and 15.0 g 1,5-cyclooctadiene in toluene, under a $N_2$ gas atmosphere at a temperature of about 0° C. The reaction mixture was stirred overnight under a nitrogen atmosphere. The formation of black nickel metal particles was observed. The yield of bis(1,5-cyclooctadiene)-Ni(O) was only about 1.0 gram, i.e., equivalent to a yield of only about 12%, based on nickel acetylacetonate. This result demonstrates that the preparation of bis(cyclooctadiene)Ni(O) from anhydrous Ni acetylaconate in the absence of added butadiene is not a feasible method.

EXAMPLE II

This example illustrates the preparation of bis(1,5-cyclooctadiene)Ni(O) from hydrated Ni(II) acetylacetonate in the absence of added 1,3 butadiene, in accordance with the process of this invention.

27 mL of a 1.9 molar solution of triethylaluminum (TEA) containing 51.3 millimoles of TEA was slowly added to a cold mixture (−78° C.) of 7.4 g (25.3 mmol) Ni(II) acetylacetonate dihydrate (99% purity) and 15.0 g (138.9 mmol) freshly distilled 1,5-cyclooctadiene in 20 mL of dry toluene. The slow addition of TEA was carried out with stirring under an argon atmosphere over a period of 15 minutes, while keeping the reaction mixture in a dry ice/acetone cold bath (at −78° C.). After the TEA addition had been completed, the cold bath was removed and the reaction mixture was stirred for 4 hours at room temperature. Thereafter, the reaction mixture was filtered, the filter cake was washed twice with 25 mL of cold toluene and then twice with 25 mL of cold diethyl ether. The bright-yellow microcrystalline product was dried under vacuum conditions.

The weight of the dried bis(1,5-cyclooctadiene)Ni(O), which melted with decomposition under an argon atmosphere at 142° C., was 6.38 g (23.2 mmol). Thus, the yield, based on Ni(II) acetylacetonate dihydrate, was 92%. No formation of black Ni metal particles was observed.

Three additional preparation in accordance with the above-described invention procedure were carried out, except that the TEA addition occurred at the following temperatures: −34° C., −18° C., and −2° to −5° C. Yields of dry bis(1,5-cyclooctadiene)Ni(O) were 92%, 91% and 91%, respectively. No formation of black nickel particles was observed.

Reasonable variations, modifications and adaptations for various conditions and reactants can be made within the scope of the disclosure and the appended claims without departing from the scope of this invention.

That which is claimed is:

1. In a process for preparing bis(1,5-cyclooctadiene)-nickel(O) from nickel(II) acetylacetonate and 1,5-cyclooctadiene in the presence of at least one alkylaluminum compound, the improvements which comprise: (a) the use of a nickel(II) acetylacetonate hydrate, (b) a molar ratio of said at least one alkylaluminum compound to said nickel(II) acetylacetonate hydrate of at least about 1.5:1, and (c) the substantial absence of added butadiene.

2. A process in accordance with claim 1, wherein said nickel(II) acetylacetonate hydrate is nickel(II) acetylacetonate dihydrate.

3. A process in accordance with claim 1, wherein said molar ratio is in the range of about 1.5:1 to about 5:1.

4. A process in accordance with claim 1, wherein said at least one alkylaluminum compound is at least one trialkylaluminum with each alkyl being independently selected from alkyl groups containing 1–8 carbon atoms.

5. A process in accordance with claim 4, wherein the molar ratio of said at least one trialkylaluminum to nickel(II) acetylacetonate hydrate is in the range of about 1.5:1 to about 5:1.

6. A process in accordance with claim 5, wherein said molar ratio if about 1.8:1 to about 2.5:1.

7. A process in accordance with claim 5, wherein said molar ratio is about 1.8:1 to about 2.5:1, and said at least one trialkylaluminum is triethylaluminum.

8. A process in accordance with claim 1, wherein the molar ratio of said 1,5-cyclooctadiene to said nickel(II) acetylacetonate hydrate is about 1:1 to about 20:1.

9. A process in accordance with claim 8, wherein said molar ratio if about 4:1 to about 8:1.

10. A process in accordance with claim 1, comprising the steps of mixing nickel(II) acetylacetonate hydrate, 1,5-cyclooctadiene and said at least one alkylaluminum compound at a temperature not to exceed about 0° C.

11. A process in accordance with claim 10, wherein said temperature is in the range of about −80° C. to about 0° C.

12. A process in accordance with claim 10, wherein said mixing is carried out for a time period of at least 1 minute under a dry, inert gas atmosphere.

13. A process in accordance with claim 10, comprising the additional step of heating the mixture comprising said nickel(II) hydrate, said 1,5-cyclooctadiene and said at least one alkylaluminum compound to a temperature of above about 0° C.

14. A process in accordance with claim 13, wherein said temperature is about 0°–50° C.

15. A process in accordance with claim 13, wherein said alkylaluminum compound is triethylaluminum, and said temperature is about 10°-30° C.

16. A process in accordance with claim 13, wherein said mixture is heated for a period of about 10 minutes to about 20 hours.

17. A process in accordance with claim 13 comprising the further step of separating formed bis(1,5-cyclooctadiene)nickel(O) from said mixture after said heating.

18. A process in accordance with claim 1, wherein an aromatic hydrocarbon is present as a solvent.

* * * * *